Figure 1:
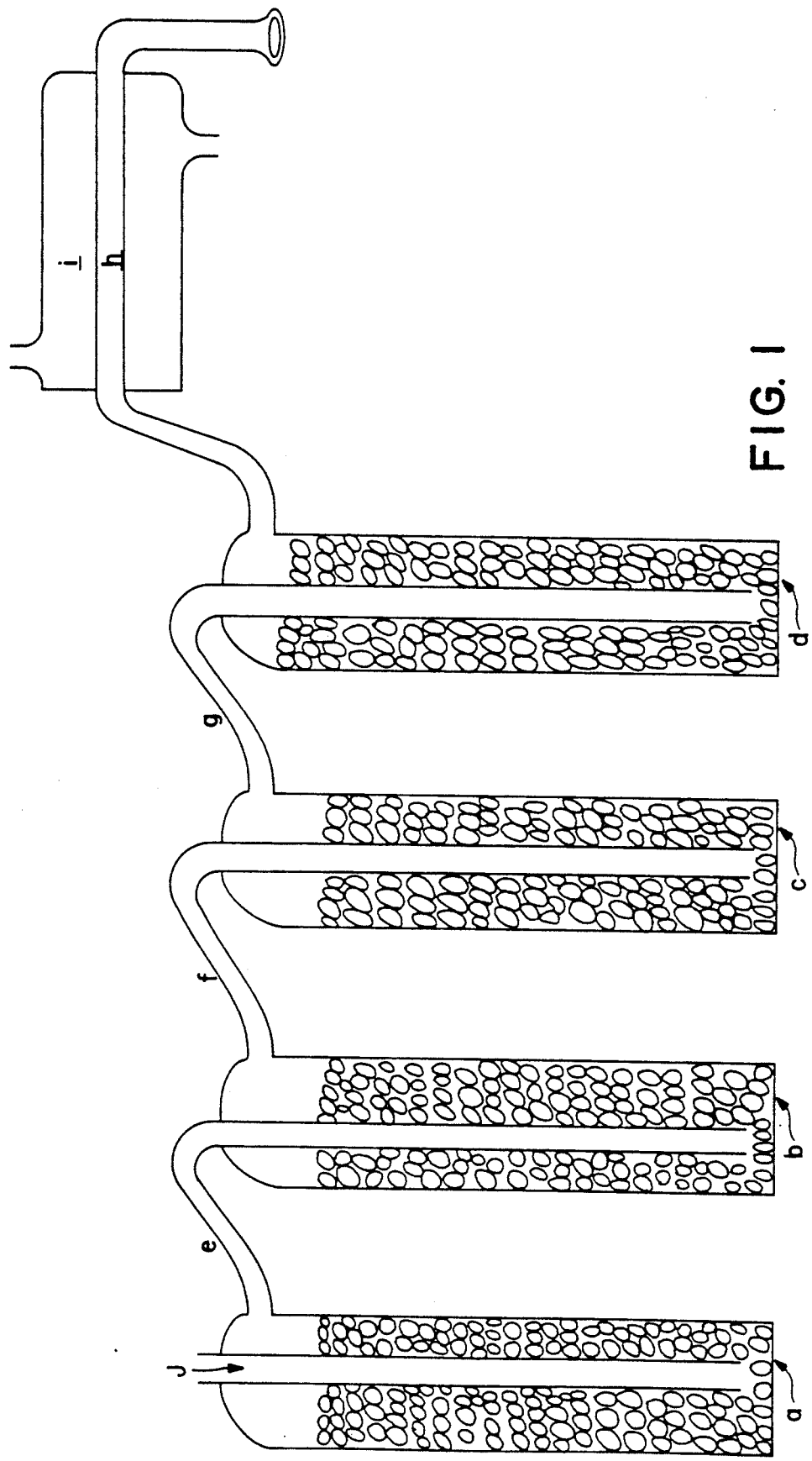
Figure 2:
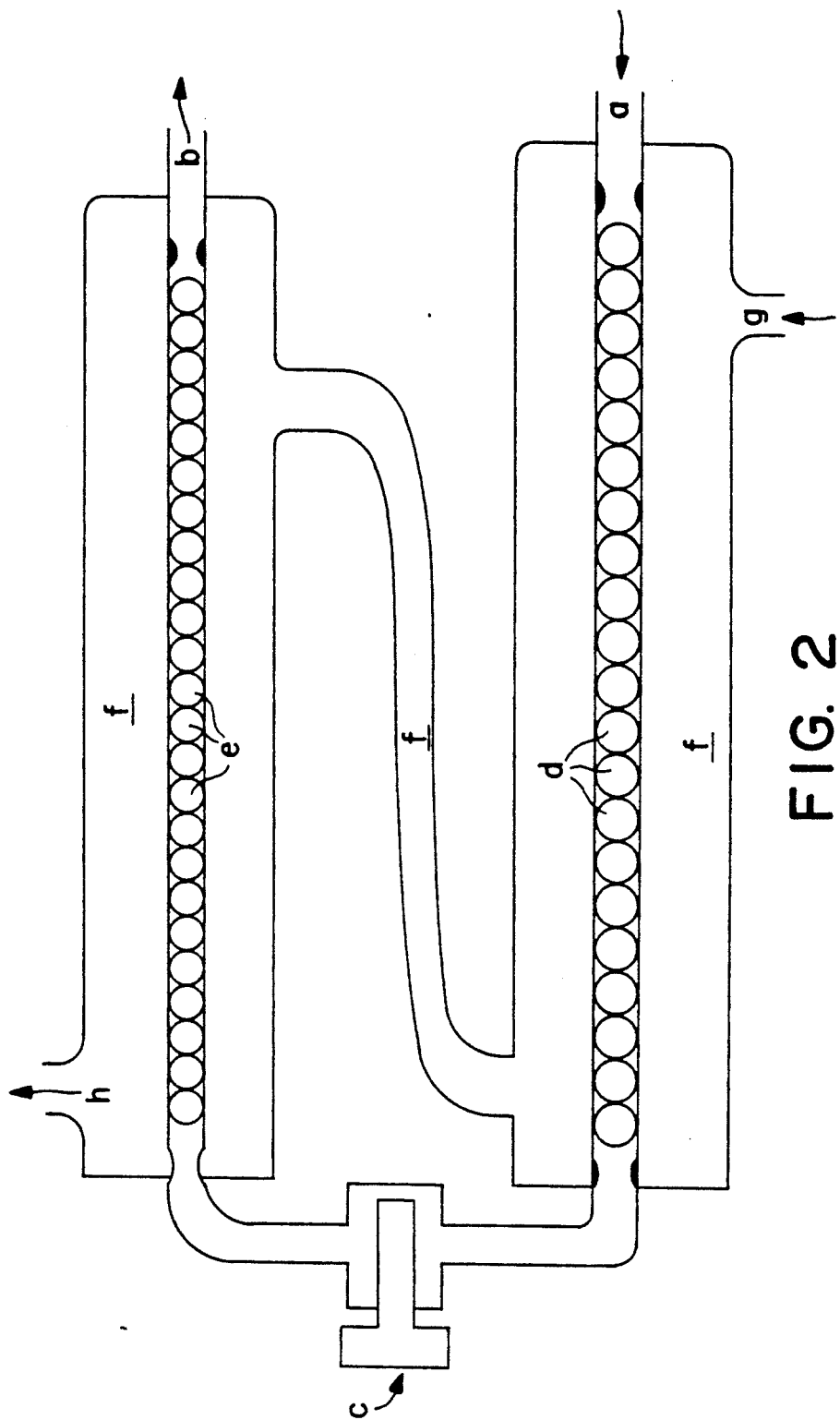

United States Patent [19]

Sanders et al.

[11] Patent Number: 5,327,779
[45] Date of Patent: Jul. 12, 1994

[54] VAPOR PRESSURE MEASUREMENT BY GAS SATURATION FOR MIXTURE

[75] Inventors: Robert N. Sanders; Robin P. McCarthy, both of Baton Rouge, La.

[73] Assignee: Ethyl Corporation, Richmond, Va.

[21] Appl. No.: 951,050

[22] Filed: Sep. 24, 1992

Related U.S. Application Data

[63] Continuation of Ser. No. 825,553, Jan. 24, 1992, abandoned.

[51] Int. Cl.⁵ .............................................. G01N 7/00
[52] U.S. Cl. ................................ 73/64.45; 73/29.01; 73/61.41
[58] Field of Search .............. 73/29.01, 53.01, 61.41, 73/64.45

[56] References Cited

U.S. PATENT DOCUMENTS

| | | | |
|---|---|---|---|
| 2,671,343 | 3/1954 | Jacobs et al. | 73/53 |
| 2,995,922 | 8/1961 | Firth et al. | 73/53 |
| 3,527,085 | 9/1970 | Silas et al. | 73/64.2 |
| 3,901,062 | 8/1975 | Lynch et al. | 73/64.2 |
| 4,395,903 | 8/1983 | Gouw | 73/64.2 |
| 4,928,515 | 5/1990 | Rosaen | 73/61 R |

OTHER PUBLICATIONS

Environmental Protection Agency Statute 40 CFR, Ch.1 (Jul. 1, 1991 Edition), §796.1950.

*Primary Examiner*—Hezron E. Williams
*Assistant Examiner*—George Dombroske
*Attorney, Agent, or Firm*—E. E. Spielman, Jr.

[57] ABSTRACT

Disclosed herein is an apparatus and process for determining the vapor pressure of materials in a mixture at relatively low vapor pressures by a gas saturation procedure. The process comprises passing an inert gas over a sampled material at a controlled flow rate to create a vapor of the sampled materials that may be collected and analyzed. Of particular importance, this method and apparatus provides a means of collecting vaporized samples over an extended period of time and, therefore, allows even minor components of mixtures to be considered in the final vapor pressure analysis. The apparatus also includes a means for determining whether sampled material has progressed as vapor beyond the means of collecting the sampled material.

13 Claims, 2 Drawing Sheets

VAPOR PRESSURE MEASUREMENT BY GAS SATURATION FOR MIXTURE

This is a continuation of copending application(s) Ser. No. 07/825,553, filed on Jan. 24, 1992, (now abandoned).

FIELD OF THE INVENTION

This invention relates to a means and a process for accurately determining the vapor pressure of materials by a gas saturation method. More particularly, this invention relates to a means and a process which allows the determination of the vapor pressure of either a single material or a mixture of materials.

BACKGROUND OF THE INVENTION

Due to the necessity for storing and shipping volatile chemicals, it has become increasingly important to determine the amount of such chemicals which may become airborne under varying conditions. As vapor pressure is an important indication of a material's volatility, it is desirable to have a means to conveniently and accurately measure the vapor pressures of a widening assortment of chemical materials. Of even greater need is such a means to measure the vapor pressures of various materials which may be found as components, even minor components, of a mixture of chemicals.

Two prior methods of determining the vapor pressure of materials were disclosed by the U. S. Environmental Protection Agency and can be seen at 40 CFR §796.1950. The methods are the isoteniscope procedure, which is used for pure liquids with vapor pressures from 0.1 to 100 kPa., and the gas saturation procedure, which is used for vapor pressures from $10^{-5}$ to $10^3$ Pa. Each of these methods provide an accurate means of determining the vapor pressure of pure compounds.

The isoteniscope method involves placing a sample of a liquid in a thermostated bulb, the isoteniscope, which is connected to a manometer and a vacuum pump. Gases which are dissolved and entrained are removed from the sample in the bulb by degassing the liquid sample at a reduced pressure. Then the vapor pressure of each sample at selected temperatures is determined by balancing the pressure caused by the sample's vapor pressure against a known pressure of an inert gas. The vapor pressure of the sample compound is tested three times at 25° C.(+ or −0.5° C.) and at any other suitable temperatures.

The gas saturation procedure requires the use of an insulated container which can maintain a constant temperature for the equipment and samples involved. The temperature inside the box is maintained at a given temperature (+ or −0.5° C.). Each sample is held in a sample holder upstream from a sorbent holder and connected to both inlet and outlet ports in the box via a small tube. Nitrogen gas, split into a number of streams equalling the number of samples present flows into the container via thin tubing. After the nitrogen reaches a thermal equilibrium, it flows through the sample and the sorbent holder and exits from the container. The flow rate of the effluent gas is checked frequently to determine the total volume of carrier gas utilized. The vapor pressure is then calculated from the total gas volume and the mass of the sample vaporized via the formula:

$$p = (w/M)(RT/v)$$

wherein p indicates the pressure (in Pascals), w indicates the transported mass of the vaporized test sample having a molecular weight of M, R is the gas constant (8.31 Pa m$^3$mol$^{-1}$K$^{-1}$), T is the temperature in degrees Kelvin and v is the volume of gas utilized.

These methods disclosed at 40 CFR §796.1950, however, have limitations. Of significance is the fact that these methods are not practical for determining the vapor pressure of various compounds that may be found in mixtures.

It has been found that samples of gases taken rapidly from a material comprising a mixture of compounds may not accurately indicate the normal vapor pressures of the minor components of the mixture. In addition, the formula used to determine vapor pressure by comparing the volume of gas used to the mass of the sample vaporized may not accurately determine the amount of vapor pressure associated with these minor components. In order to accomplish accurate sampling, it has also been found that the gaseous samples need to be collected by utilizing a considerably low flow rate of gases over the sampled liquid. While such a flow rate may be advantageous to the final vapor pressure determination, it requires extensive collection time. The methods of collecting described in the prior art are labor intensive and not practical for all applications.

Therefore, it is an object of this invention to provide a means of accurately determining the vapor pressure of not only pure compounds, but also of the components of compounds found in mixtures. It is also an object of this invention to provide a means by which gaseous samples necessary for the determination of a substances vapor pressure can be collected over an extended period of time without requiring an undesirable amount of human effort.

SUMMARY OF THE INVENTION

The present invention provides a means of accurately collecting samples of material as vapor to allow the determination of the materials vapor pressure under varying conditions. Of significant importance is this invention's ability to assist in the determination of the vapor pressure of not only pure compounds, but also of those compounds found in mixtures. With advancing concerns regarding the handling, storage, and environmental implications of various compounds, this invention provides a beneficial and accurate means to ascertain vapor pressures created by materials providing only a minor portion of the vapor pressure in a mixture.

As with prior methods, in order to determine the vapor pressure of a particular substance, it is necessary to create a vapor phase containing the desired substance in concentrations that will reliably indicate its natural vapor pressure under various conditions. In order to ensure that the minor components of a mixture are correctly represented, it has been found that the rate at which the vapor is created is of considerable importance. A rapid vaporization, caused by a hurried collection of the sampled material into the vapor phase, will not necessarily collect reliable amounts of minor components. Similarly, a rapid transfer of the collected vapor to analyzing equipment does not ensure a trustworthy determination. A hurried collection of sampled material into a vapor phase may pick up more than mere vapor. It may include small particulate portions found over the sample that can skew the percentages of each component in the vapor phase.

These problems can be eliminated by creating a system in which the sampled material is slowly collected into a vapor phase. This is accomplished by gradually passing an inert gas over an extended surface area in contact with the sampled material. By controlling the rate of collection of sample into the vapor and the means used to collect the desired substances from the vapor, it has been found that more reliable data can be collected. This controlled collection allows the accurate analysis even of samples which have very low vapor pressures, such as below 0.1 mm Hg, whether from pure compounds or as part of a mixture of compounds.

The material to be sampled may be collected into a vapor phase in any manner which will insure that no contamination from other sources will enter the vapor phase. It is self-evident that all components of this system be inert as related to the sampled material and the final vapor collected. Also apparent is the need to maintain strict temperature and pressure controls on the sample and gas carrying the sample as the sample is collected and transported through the system of this invention.

It is preferred that the collection of the sample material be conducted by passing an inert gas over the sampled material at a controlled temperature and pressure representing the conditions for which the specific vapor pressure is sought. It is more preferred that the inert gas which will carry the vapor be passed through the sample. It is most preferred that the inert gas be passed through the sample via a means that will increase the surface area contact between the sample and the carrying gas. A vertical packed bed arrangement is quite advantageous to this end.

Any packing that creates a surface area which will sufficiently introduce the inert gas to the sample material may be used. Packing materials such as beads, pellets, wire mesh, etc. may be used. Commercially available packing materials such as screens, pall rings, Raschig rings, Lessing rings, tellerettes, Berl saddles, Koch Flexipac packing, Intalox saddles, etc., may also be used to divert the carrying gas as it passes through the sampled material. For ease of handling and replacement, it has been found that beads, such as glass beads, are preferred for working with many types of materials.

To protect the integrity of the final results it is necessary that the carrying gas and the sampled material be maintained at an acceptable range of temperatures and pressures. While most tests are likely to be carried out at ambient pressure, commercially available devices for controlling pressure can be incorporated with the present invention without deviating from its intended functions.

Temperature regulation may also be carried out by a number of commercially available means. It is preferred that the temperatures be maintained to within about one half degree Centigrade of the desired temperature. It is more preferred that the temperature be held to within about one tenth degree Centigrade of the temperature sought. In order to accomplish this, the practice of the present invention can be carried out in a thermally controlled container, which may prove beneficial for desired temperatures considerably above or below ambient temperatures. For ease of handling at temperatures closer to normal room conditions, a liquid bath may be utilized. Baths containing water or a mixture of water and ethylene glycol may provide an easy and economical way to regulate the system. The practice of this invention is not limited to any particular type of thermally controlling device. It may be conducted in any container which allows adequate control of the desired temperature(s). Likewise, the practice of the present invention is not limited to any particular temperature range. The present invention can be adapted to any particular temperature range over which a sampled material may be stored or shipped.

Once the sampled material has been obtained in a true vapor it becomes necessary to collect the material. Analysis of the vapors contents can then be conducted by contemporary methods such as gas chromatography and mass spectrography gas chromatography.

Collection of the sampled material from the vapor may be conducted in any noncontaminating manner which lends itself to a final analysis of the collected material. Of preference with the present invention is a condensing apparatus which condenses the sampled material onto a surface, from which it can be readily removed. More preferred is a collecting mechanism by which the sample is thermally condensed onto a packing material, similar to those previously mentioned. The sample can be easily removed from this packing by a solvent which lends itself to a final system for analyzing the collected sample(s). For ease and convenience, it has been most preferred that the sampled vapor be thermally condensed onto a series of glass beads. Not only do the beads provide an adequate surface for condensation, but they are also easily adaptable when the amount of sample to be collected increases.

In many mixtures the amounts of minor components may be only a small percentage of the total mixture. In order to collect enough of such minor components to analyze and to allow a molecular weight determination on the vapor from mixtures, a sizeable amount, as much as 50 mg or more, of the vaporized sample must be collected. To insure that all of the vapor is collected, an extensive amount of cooled surface area may be needed. The packings listed, especially the preferred glass beads, easily lend themselves to this requirement as the collector can be readily expanded by one familiar with the art.

It is preferred that an additional condenser-type collecting unit be placed at terminal end of this system following the actual sample collecting stage. This extra mechanism then serves as a check on the accuracy of the collection when it is completed.

If the system is used as intended, the flow of gas and the amount of sampled material passed through the system will allow all of the sampled vapor to be condensed on the intended collector. However, if the operator of the system miscalculates the desired conditions and allows additional vapor to pass beyond the intended collecting site, some components of the vaporized sample may be lost and not included in the resulting test data. The additional collecting unit would, in such cases, collect at least a portion of any overflowing vapors. This additional collector then serves as a safety check on a particular test's accuracy. Additional sampled material found on the second condenser then indicate to an operator that the system must be rechecked before the resulting data is reliable.

It is preferred that the system of this invention be continuous from the sample vaporizing step to the collection step and additional condenser. Such a continuous system not only allows for longer testing schedules without the need for human interference, but also helps secure the system from any contamination that may occur from careless handling.

The continuous nature of the system also allows for a single set of gas flow devices to be used for the entire system. The initial flow of inert gas which vaporizes the sampled material can then be used to carry the resulting vapor over through to the condenser-type collector and then pass through an additional collecting device.

As mentioned above, regulating the flow of inert gas, and the resulting vaporized sample, through the system is imperative to provide a final recovered sample that leads to an accurate analysis. The rate of flow can be varied higher or lower for differing samples, but it is preferred that the flow rate of gas be between about 0.8 and about 3.0 ml/minute. It is most preferred that this rate be between about 1.0 and about 1.5 ml/minute. This flow rate can be controlled by commercially available devices. Examples of such devices are the Mass Flow Meter Type 258C/1258C/2258C, made by MKS, and the Edwards Model 825 Mass Flow Controller. These devices can also be measured and controlled by contemporary devices, such as the MKS Type 247C 4 Channel Readout and the Edwards Diametrics Controller 1605.

Diagrams

While not limiting to the present invention, the attached diagrams 1 and 2 are intended to help demonstrate the use of this invention. It is understood that the present invention may be subject to adjustments in and from the equipment depicted in the diagrams provided without deviating from the subject matter claimed herein.

Diagram 1 indicates a cross-sectional view of the container in which the sampled material is vaporized and a series of containers housing packing materials, in this case beads, which create a large surface area over which to pass the vaporized sample. Containers "a" "b" "c" and "d" would rise vertically and contain the sampled material in their lower portions. As an inert gas if flowed through opening "j", its pressure would carry it through the packing to vaporize some of the sampled material in container "a." The vaporized material would then be carried by the flow of inert gas through the packing materials and sampled material of containers "b" "c" and "d" via the conducting tubes "e" "f" and "g" to allow a slow vaporization of the sample in the inert gas. The vapor would then be carried out of the system via a conducting means, as demonstrated by tube "h" to a collecting means, as demonstrated by the condenser labelled "i".

Diagram 2 provides an illustration of the condenser-type collecting means and the additional condensing means preferred as an aspect of the present invention.

As the "cleansed" sample vapor passes from the system it enters the thermal condensation collector via opening "a" and passes over the beads, "d" upon which the vapor is to be condensed. A cooling fluid passing through condenser "f" via openings "g" and "h", would facilitate this collection. The inert gas then passes through valve "c" to the beads, "e", of the additional condenser used as a safety check on the system. Any additional condensation occurring in this latter stage is also facilitated by the use of the cooling fluid passing through condenser "f".

We claim:

1. An apparatus for determining the vapor pressure of a sampled material comprising:
    a) a means of containing and passing an inert gas through said apparatus at a controlled rate,
    b) at least one means of controlling and maintaining the temperature of said inert gas and sampled material throughout the apparatus,
    c) at least one container housing said sampled material and providing a surface area which allows a means of contacting said inert gas with said sampled material to cause the sampled material to be held as a vapor in the inert gas,
    d) a means of collecting the sampled material which has been held as vapor in the inert gas, and
    e) a means of determining whether additional sampled material has progressed as vapor beyond the means of collecting the sampled material.

2. The apparatus of claim 1 in which the surface area which allows a means of contacting said inert gas with said sampled material is provided by packing materials in the container(s).

3. The apparatus of claim 2 in which the packing materials in the container(s) are glass beads.

4. The apparatus of claim 1 in which the means of controlling the temperature of said sample and inert gas comprises a thermally controlled container encompassing the apparatus.

5. The apparatus of claim 4 in which the thermally controlled container is an oven.

6. The apparatus of claim 1 in which the means of controlling the temperature of said sample and inert gas comprises a thermally controlled liquid bath.

7. The apparatus of claim 6 in which the thermally controlled liquid bath is a water bath.

8. The apparatus of claim 7 in which the water bath contains a mixture of water and ethylene glycol.

9. The apparatus of claim 1 in which the means of controlling the temperature of the inert gas and sampled material throughout the apparatus is capable of maintaining the temperature to within about one half degree Centigrade of that desired.

10. The apparatus of claim 1 in which the means of controlling the temperature of the inert gas and sampled material throughout the apparatus is capable of maintaining the temperature to within about one tenth degree Centigrade of that desired.

11. The apparatus of claim 1 in which the means of collecting said sampled material which has been held as a vapor in the inert gas comprises a means of thermally condensing the sampled material which has been held as a vapor onto a surface.

12. The means of collecting the sampled material of claim 11 in which the surface onto which the sampled material is condensed is a series of beads.

13. The apparatus of claim 1 in which the means of determining whether additional sampled material has progressed as vapor beyond the means of collecting the sampled material comprises an additional means of thermally condensing any remaining sampled material onto a surface.

* * * * *

UNITED STATES PATENT AND TRADEMARK OFFICE
CERTIFICATE OF CORRECTION

PATENT NO. : 5,327,779
DATED : July 12, 1994
INVENTOR(S) : Robert N. Sanders; Robin P. McCarthy It is certified that error appears in the above-identified patent and that said Letters Patent is hereby corrected as shown below:

On title page, item [54] line 2, and col. 1, line 2, "Mixture" should read --Mixtures--.

Column 6, Line 55, reads " . . . means of collecting the sampled material . . . and should read -- . . . apparatus . . . --.

Signed and Sealed this

Twenty-seventh Day of September, 1994

Attest:

BRUCE LEHMAN

Attesting Officer         Commissioner of Patents and Trademarks